United States Patent [19]

Meyer

[11] Patent Number: 5,874,268
[45] Date of Patent: Feb. 23, 1999

[54] METHOD OF INTRODUCING EXOGENOUS COMPOUNDS INTO CELLS BY ELECTROPORATION AND APPARATUS FOR SAME

[75] Inventor: Tobias Meyer, Durham, N.C.

[73] Assignee: Duke University, Durham, N.C.

[21] Appl. No.: 718,658

[22] Filed: Sep. 23, 1996

[51] Int. Cl.⁶ .................................................. C12N 13/00
[52] U.S. Cl. ..................................... 435/173.6; 435/173.5
[58] Field of Search .............................. 435/173.5, 173.6

[56] References Cited

U.S. PATENT DOCUMENTS

| | | | |
|---|---|---|---|
| 4,882,281 | 11/1989 | Hilliard et al. | 435/285.2 |
| 5,128,257 | 7/1992 | Baer | 435/173.6 |
| 5,349,053 | 9/1994 | Landolfi | 530/351 |
| 5,420,264 | 5/1995 | Seed et al. | 536/23.5 |
| 5,422,272 | 6/1995 | Papp et al. | 435/285.2 |
| 5,512,457 | 4/1996 | Lyman et al. | 435/69.5 |
| 5,550,054 | 8/1996 | Witte et al. | 435/240.2 |

FOREIGN PATENT DOCUMENTS

| | | |
|---|---|---|
| 0126786 | 10/1989 | Japan. |
| 08322548 | 12/1996 | Japan. |

OTHER PUBLICATIONS

McCormick et al. (1992) J. Chem. Tech. Biotechnol., 54(2), "A Low Cost Microprocessor–Controlled Electrofusion and Electroporation System", pp. 159–169.

Lewin (1987) Genes (Third Edition), John Wiley & Sons, New York, p. 736.

*Primary Examiner*—Jon P. Weber
*Attorney, Agent, or Firm*—Myers Bigel Sibley & Sajovec

[57] ABSTRACT

An electroporation apparatus for introducing exogenous material into cells is described herein. The apparatus comprises first a base member (15) configured for holding a cell support, the cell support having a top surface portion, with the top surface portion configured for carrying adherent cells. The apparatus further comprises an electrode carrier (25) operably associated with the base member, the electrode carrier having a bottom surface portion, a first electrode (30) connected to the electrode carrier, and a second electrode (35) also connected to the electrode carrier. The electrode carrier has a channel (40) formed therein, with the channel positioned between the first electrode and the second electrode, so that exogenous material may be introduced through the channel and into contact with the cells. Methods for introducing exogenous compounds into a cell and for visually detecting the location of binding events within a cell are also disclosed.

9 Claims, 10 Drawing Sheets

METHOD OF INTRODUCING EXOGENOUS COMPOUNDS INTO CELLS BY ELECTROPORATION AND APPARATUS FOR SAME

This invention was made with Government support under grants GM-48113 and GM-51457 from the National Institutes of Health. The Government has certain rights to this invention.

FIELD OF THE INVENTION

This invention relates to a method of introducing exogenous compounds into cells by electroporation.

BACKGROUND OF THE INVENTION

Single cell assays to measure signal transduction and other cellular processes are useful for the identification of drug targets, as well as for drug screening. The number of known signaling molecules involved in particular cell functions and disease states is rapidly increasing. At the same time, combinatorial chemistry has dramatically expanded the number of substances that must be tested for their effect on specific signaling molecules and transduction pathways. Commonly used in vitro measurements of drug-target binding interactions and other screening methods are often inadequate to assess the effectiveness of drugs within the cellular context, and therefore, the ability to assay intact cells for particular cell functions would be a powerful way to investigate all signaling steps that lead to the monitored event. Currently, the main limitations for this strategy are: (i) the lack of an efficient method to rapidly introduce membrane impermeant molecules into adherent cells using cost efficient amounts of samples and (ii) the limited number of available single cell assays to test for particular cell functions.

SUMMARY OF THE INVENTION

A first aspect of the present invention is an electroporation apparatus for introducing exogenous material into cells. The apparatus comprises a base member configured for holding a cell support, the cell support having a top surface portion, the top surface portion configured for carrying adherent cells; an electrode carrier operably associated with the base member, the electrode carrier having a bottom surface portion; a first electrode connected to the electrode carrier; and a second electrode connected to the electrode carrier. The electrode carrier has a channel formed therein, with the channel positioned between the first electrode and the second electrode, so that the exogenous material may be introduced through the channel and into contact with the cells.

A second aspect of the present invention is a method for introducing an exogenous compound into cells The method comprises providing a cell support, with said cell support having a top surface portion with the cells adhered thereto, and with the cells being in contact with (i.e., immersed in) an electroporation solution; positioning a pair of electrodes in said electroporation solution; positioning a micropipette between the pair of electrodes, with the micropipette having an outlet opening that is in fluid contact with the electroporation solution; introducing the compound through the outlet opening and into the electroporation solution; and subjecting the cells to a current pulse across the pair of electrodes, the current pulse sufficient to cause the compound to pass through the cell membranes of the cells and into the cells by electroporation.

A third aspect of the present invention is a method for visually detecting the location of binding events within a cell. The method comprises introducing a fusion protein into the cell, the fusion protein comprising a binding domain and a detectable domain; and then visually detecting the location of increased levels of the detectable domain within the cell, the location of increased levels of the detectable domain indicating the location of a compound within the cell to which the binding domain specifically binds.

BRIEF DESCRIPTION OF THE DRAWINGS

In the drawings which form a portion of the original disclosure of the invention.

DETAILED DESCRIPTION OF THE INVENTION

Figure 1A:
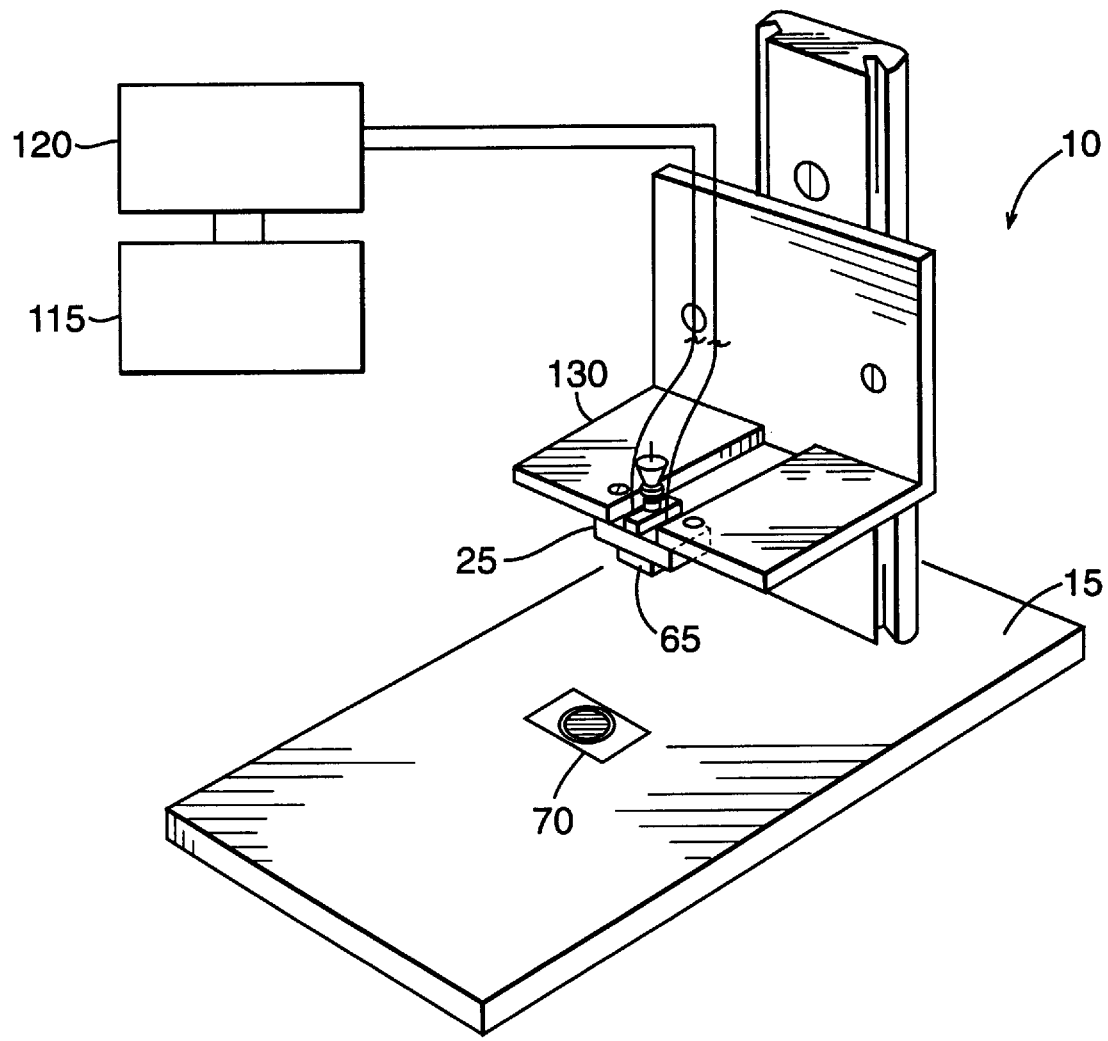
FIGS. 1a and 1b are perspective and schematic views of the electroporation apparatus of the invention.

As noted above, the present invention provides a method for introducing an exogenous compound into cells. compound. The method comprises:

(i) providing a cell support, with said cell support having a top surface portion with cells adhered thereto, and with said cells being in contact with an electroporation solution;

(ii) positioning a pair of electrodes in said electroporation solution;

(iii) positioning a micropipette between said pair of electrodes, with said micropipette having an outlet opening in fluid contact with said electroporation solution;

(iv) introducing said compound through said outlet opening and into said electroporation solution; and (v) subjecting said cells to a current pulse across said pair of electrodes, said current pulse sufficient to cause said compound to pass through the cell membranes of said cells and into said cells by electroporation.

Any suitable compound may be introduced into a cell by the instant invention, including RNA, DNA, proteins, peptides, and small organic molecules. The present invention is particularly advantageous for introducing oligonucleotides, such as antisense oligonucleotides, or other compounds that are cell membrane impermeant. The method may be used to introduce a fusion protein comprised of a binding domain and a detectable domain, as discussed in detail below.

Electroporation solutions, electrode materials, and the electrical parameters for carrying out electroporation are either known to those skilled in the art or will be readily apparent in light of the disclosure set forth herein.

Micropipettes useful for carrying out the invention include any syringe or injection device that discharges a small sample volume (typically as a liquid suspension of the compound of interest) through an outlet opening, with capacities for discharging 100, 50, 25, 10, 5, 2 or 1 microliters or less (and not more than the indicated capacity) being illustrative. Smaller sample volumes are generally preferred.

The methods described herein are particularly advangateously employed in carrying out a method for visually detecting the location of binding events within a cell. Such a method comprises:

(a) introducing a fusion protein into said cell, said fusion protein comprising a binding domain and a detectable domain (e.g., a fluorescent protein); and then (b) visually detecting the location of increased levels of said detectable domain within said cell, the location of increased levels of said detectable domain indicating the location of a compound within said cell to which said binding domain specifically binds.

While the introducing step may be carried out by introducing RNA encoding the fusion protein into said cell, wherein said fusion protein is translated from said RNA, the introducing step may also be carried out by introducing the fusion protein directly into the cell. Further, while the fusion protein (or RNA encoding the same) may be introduced by the methods and apparatus described herein, the fusion protein (or RNA encoding the same) may also be by other suitable techniques, such as microparticle bombardment.

Suitable detectable domains include fluorescent proteins, such as green fluorescent protein (GFP), apoaequorin, and analogs and derivatives thereof. Green fluorescent protein is derived from the jellyfish *Aequorea victoria* and has been expressed in a wide variety of microbial, plant, insect and mammalian cells. A. Crameri et al., *Nature Biotech.* 14, 315–319 (1996). Any detectable domain may be employed, and other suitable detectable domains include other fluorophores or fluorescent indicators, such as a fusion tag with any binding domain such as avidin, streptavidin and ligand binding domains of receptors. Coupling of biotin or other ligands to the fluorophore or indicator of interest using a dextran matrix or other linker system. Visually detectable detectable domains are preferred (e.g., those that can generate a signal that can be displayed on a visual monitor, on film or photographs, through a microscope, etc.).

Methods employing the introduction of fusion proteins into a cell, as described above, are useful in a variety of different techniques. For example, the method can be an assay for tyrosine phosphorylation, and said binding domain a tyrosine kinase Syk or a fragment thereof that binds to the FceRI receptor. The method can be an assay for diacylglycerol and the binding domain the Cl fragment of protein kinase C or a fragment of said Cl fragment that binds to diacylglycerol. The method can be an assay for nuclear translocation or transcriptional activation, and said binding domain CaM-Kinase IV. The method can be an assay for cell secretion, and the binding domain catalase. The foregoing are illustrative, and many other applications of the instant invention will be readily apparent to those skilled in the art.

Figure 1B:
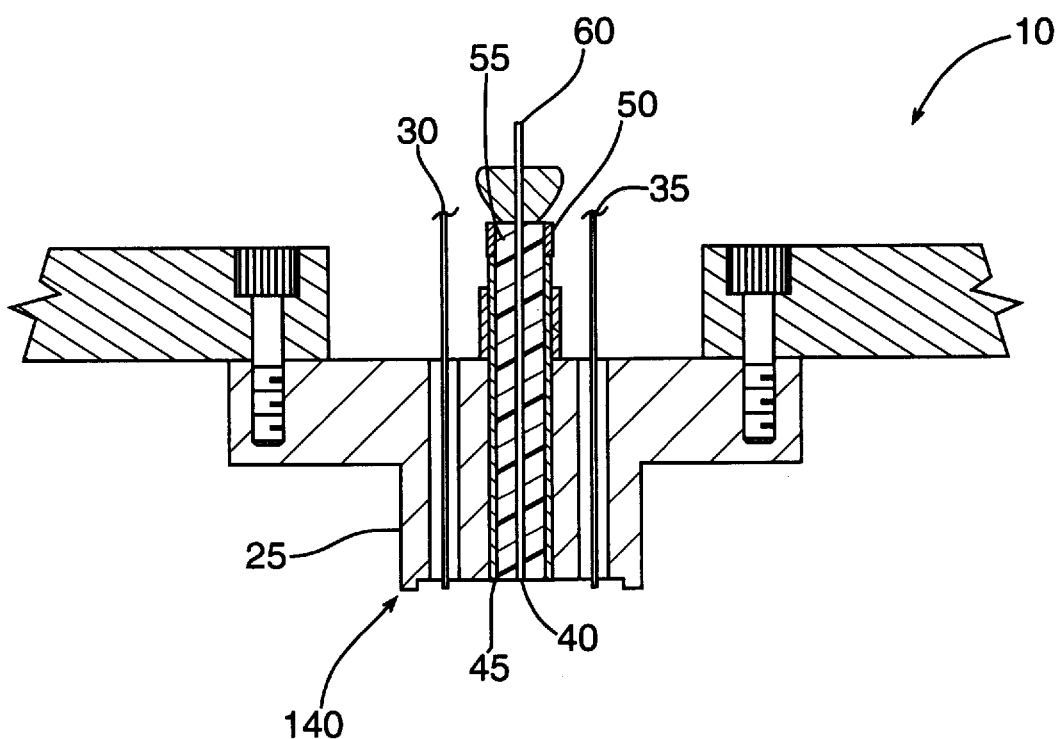
Figures 2A, 2B:
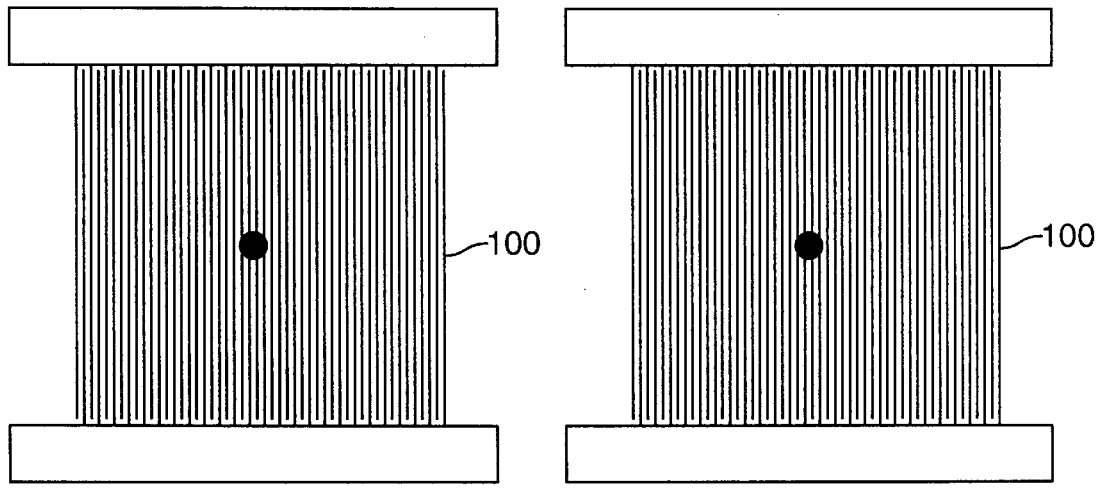
FIGS. 2a–2d are views of interdigitated electrodes of the invention.
Figures 2C, 2D:
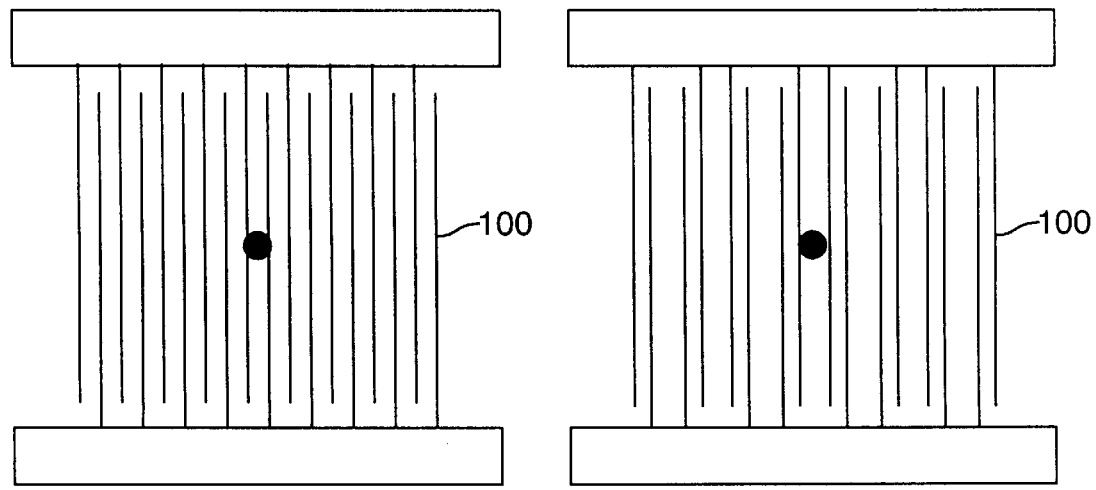

The electroporation apparatus 10 will now be described in detail and is illustrated in FIGS. 1a and 1b. The electroporation apparatus 10 is designed to introduce exogenous material into cells. Specifically, the apparatus includes a base member 15 configured for holding a cell support. The cell support has a top surface portion which is generally flat for carrying adherent cells. A cover glass for the support may be used with a 25 mm circle micro cover slide of Model No. 19063 sold by VWR Scientific of Media, Pa. being preferred. The surface portion may be made from glass or plastic. A ring made of delrin® or another appropriate polymer may be present on the cell support to carry a buffer solution. An electrode carrier 25 is operably associated with the base member 15 and has a bottom surface portion which is generally flat. The electrode carrier is most preferably made of DECRIN® polymer but may be constructed of any appropriate material, preferably a polymeric material. The electrode carrier 25 is connected to first 30 and second 35 electrodes creating an electric field which impacts the cells. The structures of the two electrodes are various and include, for example, wires and sheets. Sheet electrodes are preferred since they have been found to minimize inconsistencies which may exist in the electric field. The electrodes 30 and 35 are preferably spaced between about 3 mm to 5 mm apart, and are more preferably about 4 mm apart. The electrodes can be formed from a number of appropriate materials, and are preferably formed from platinum. The electrodes are designed to preferably accommodate a peak voltage of 200 to 400 V with an RC discharge time constant in the 10 to 500 ms range. Slightly different field strengths may be required depending on the type of cells used. It is especially preferred that the electrodes be positioned with the carrier to be generally parallel to one another.

In accordance with the invention, a channel 40 is formed within the electrode carrier 25 and is positioned between the first and second electrodes 30 and 35 as illustrated in FIG. 1b. The channel 40 allows for exogenous material to be introduced through the channel and into contact with the cells. Specifically, stainless steel tubing 45 is inserted into the channel 40 and serves as a guide. Commercially preferred tubing is Model No. A-HTX-B sold by the Lee, Company of Essex, Conn. and has an inner diameter of 0.071 inch and an outer diameter of 0.095 inch. A threaded steel sleeve 50 extends around the outer diameter of the top of flexible tubing 55 with Model No. TMCA 32020302 being preferred. The flexible tubing 55 is present within the stainless steel tubing which facilitates the transport of the exogenous material to the cells. In particular, the flexible tubing serves as a micropipette. Teflon® tubing of Model No. TUTA 1226930L sold by Small Parts, Inc. of Miami Lakes, Fla. is especially preferred, having an inner diameter of 0.012 inch and an outer diameter of 0.065 inch. A wire 60 is used as a plunger within the Teflon® tube to inject the exogenous material with Model No. A-SWGX-120 sold by The Lee Company. The wire 60 is used to insert a variety of materials such as, for example, proteins, dextrins, and other agents. Various volume sample sizes such as those less than 100 µl, less than 50 µl, less than 25 µl, less than 10 µl, 5 µl or less, between 1 and 2 µl, and more typically less than 1 µl may be injected by the wire.

The electrode carrier 25 is connected to a bracket, which bracket is connected by a pair of linear bearings which are in turn connected to a double rail track. The double rail track and bearings are sold commercially by TECHNO Linear Bearing of New Hyde Park, N.Y. The preferred bearing has catalog number HL 4500M222001 and the preferred double rail has a catalog number HL 4222M0010300.

Cushioning means 70 such as a foam pad for example, is positioned between the base member 15 and the cell support for facilitating the generally parallel orientation of the cell support top surface portion and the electrode carrier bottom surface portion. Various appropriate cushioning means may be used for the purposes of the invention.

In one embodiment, the first and second electrodes may be members of an interdigitated set of electrodes 100 as illustrated in FIGS. 2a–2d. As illustrated, the members are configured in various grid porator designs with the distance between grid lines being of various values, namely 60 μm, 120 μm, 200 μm, along with the combination of 120 μm and 340 μm. The grid porator may be formed on the bottom of the electrode carrier.

The electroporation apparatus may also include a power supply 115 and a controller 120 operably associated with the power supply and the first and second electrodes. The power supply 115 charges a capacitor that provides a voltage and corresponding current between the electrodes. A preferred power supply is sold by BIORAD as Model 1000/500. A capacitor and relay system may also be employed providing, for example, 200–400 volts per cm. The capacitor and relay system is controlled by a personal computer equipped with a relay board.

It is useful to measure the current during electroporation of cells with the exogenous compound. For example, a detection of an increase in current may indicate that the leveling is not flat or that the ionic strength of a buffer solution is not correct. A decrease in current may indicate that air bubbles exist in the fluid transporting the exogenous material or that the first and second electrodes are corroded.

In an alternative embodiment, the electroporation apparatus may further comprise a well member 130 having an opening formed therein. The opening is defined by walls configured for receiving the electrode carrier. The well member has a bottom surface configured for contacting to the cell support top surface portion, so that the walls enclose the electroporation chamber.

Preferably, the electroporation apparatus further includes positioning means 140 for maintaining the electrode carrier bottom surface 65 in a spaced relationship to the cell support top surface. As a result, an electroporation chamber is defined therebetween. The channel formed in the electrode carrier is in fluid communication with the electroporation chamber. Preferably, the positioning means is configured for maintaining the electrode carrier bottom surface portion and the cell support top surface portion not more than 100 μm apart. The positioning means may include, for example, a lip peripheral edge portion which is positioned below the electrode carrier which is preferably spaced 100 μm from the bottom of the electrode carrier. The lip has formed therein two opposing elliptical openings which allow for the insertion of the first and second electrodes. In the center of the lip, an opening is formed which is sized to accommodate the stainless steel tubing. The lip is made from appropriate electrically non-conductive polymeric material. Other appropriate positioning means include any suitable structure on the electrode carrier or base member which allows for the proper spacing.

The present invention is illustrated in greater detail in the following non-limiting Examples. In the following Examples, mM means millimoles; nM means nanomoles, μM means micromoles; °C. means degrees Centigrade; μL means microliters; μg means micrograms; ATP means adenosine triphosphate; $cm^2$ means centimeters squared; $μm^2$ means micrometers squared; s means seconds; ms means milliseconds; nm means nanometers; mm means millimeters; W means watts; mW means milliwatts; UV means ultraviolet.

EXAMPLE 1

Generation of Transcription Vectors for Wildtype GFP, Cycle 3 Mutant GFP, and K-ras 4B GFP Vector pXen2 containing the 3' untranslated region (UTR) of *Xenopus laevis* β-globin gene was provided by Dr. Kevin Peters (Duke University). Plasmids for wildtype GFP (pRAY1) and Cycle 3 mutant of GFP plasmid (pBAD-GFP) were obtained from Dr. Donald Lo (Duke University) and Affymax (Palo Alto, Calif.), respectively. cDNA encoding human K-ras 4B was provided by Dr. Patrick Casey (Duke University).

The 3' untranslated region of the *Xenopus laevis* β-globin gene was cloned into the in vitro translation vector pSPUTK (Stratagene, La Jolla, Calif.) using the restriction sites EcoRI and BamHI. An ApaI site was introduced into the wildtype GFP by PCR with the primer 5'-CAACGGGCCCAA ATGAGTAAAGGAGAAGAAC-3' (SEQ ID NO:1) (containing the ApaI site) as the sense primer, and the SP6 primer 5'-GCATTTAGGTGACACTATAG-3' (SEQ ID NO:2) as the antisense primer. The plasmid pRAY1 was used as a template. The PCR fragment was cloned into the ApaI and XbaI sites of the modified pSPUTK vector, resulting in the transcription vector pHIROwt. This vector contains the wildtype GFP followed by the 3' UTR of β-globin.

Additional restrictions sites (ApaI and XbaI) were introduced into the cycle 3 GFP mutant by PCR (sense primer 5'-CAACGGGCCCATATGGCTAGCAAAGGAG-3' (SEQ ID NO:3); antisenseprimer: 5'-CAACTCTAGATT ATTTGTAGAGCTCATCC-3' (SEQ ID NO:4)). The plasmid PBAD-GFP was used as a template. In the same cloning step, the EcoRI site located in the 3' end of the gene was deleted by mutagenesis. Replacement of the wildtype GFP in the vector pHIROwt with the cycle 3 GFP resulted in the in vitro transcription vector pHIR01.

K-ras 4B was cloned into vector pHIR01 (K-ras 4B/pHIR01) by adding additional BamHI sites to both ends of the gene by PCR (sense primer: 5'CAACGG ATCCATGACTGAATATAAACTTGTG-3' (SEQ ID NO:5); antisense primer: 5'-GTTGGGATCCTTAC ATAATTACACACTTTGTC-3' (SEQ ID NO:6)).

EXAMPLE 2

In vitro Transcription and RNA Processing

Plasmids were linearized downstream from the 3' UTR with either SacI (pHIROwt), EcoRI (pHIR01) or ClaI (K-ras 4B/pHIR01). In vitro transcription with SP6 RNA polymerase was per formed according to the manufacturer's protocol using a commercial kit (mMESSAGE mMACHINE®, Ambion, Austin, Tex.). 10 mM EDTA was used to terminate the reaction. The RNA was purified by column chromatography (RNeasy® column, Qiagen, Chatsworth, Calif.) followed by the addition of the poly-A tail. Polyadenylation was carried out for 30 minutes at 37° C. in a 50 μl reaction mixture containing 40 nM Tris-HCl (pH 8.0), 10 mM $MgCl_2$, 2.5 mM $MnCl_2$, 250 mM NaCl, 0.25 μg/μL RNA, 250 μM ATP, and 5 units poly(A) polymerase (Life Technologies, Gaithersburg, Md.). The reaction was terminated by the addition of 20 mM EDTA. Unincorporated ATP and salt were removed by applying the mRNA to a RNeasy column. The eluent was dried and mRNA was dissolved at 2 μg/μl in electroporation buffer (5 mM KCl, 125 mM NaCl, 20 mM HEPES pH 7.4 and 10 mM glucose).

EXAMPLE 3

Cell Culturing and Electroporation

RBL 2H3 cells were maintained in Dulbecco's Minimum Essential Medium (DMEM) supplemented with 20% fetal bovine serum (Life Technologies, Gaithersburg, Md.) at 37° C. with 5% $CO_2$. The cells were plated at $5 \times 10^4$ cells/cm$^2$ on glass cover slips, and were allowed to attach to the coverslip for at least 3 hours. A small-volume electroporation device for adherent cells was used for electroporation. After replacement of the medium in the dish with electroporation buffer, the mRNA sample was applied (1 μl at 1–2 μg/μl). Electroporation was performed at 350 V/cm, using 3 voltage pulses, each 40 ms long and 40 s apart. After electroporation, the electroporation buffer was replaced with DMEM (without phenol red). Until observation, cells were kept at 37° C. for cycle 3 GFP and at 30° C. for wildtype GFP. The lower temperature was necessary to observe sufficient wild-type GFP fluorescence.

EXAMPLE 4

Marking of GFP by UV-laser Pulses

GFP-elecgtroporated cells were monitored using an Odyssey confocal imaging system (Noran Inc., Middleton, WI) mounted on an inverted Nikon Diaphot microscope. In combination with a Raptor Imaging board (Bitlow, Woburn, Mass.) and Eye Image Calculator software (IO Industries, London, Ontario, Canada), this system captures images every 16.7 ms. GFP fluorescence was excited at 488 nm and was monitored above 495 nm. GFP was locally marked by using a focused UV-laser (365 nm; Enterprise, Coherent Inc., Palo Alto, Calif.). The UV-laser was coupled into the optical axis through the fluorescence microscope port using a UV-reflecting dichroic mirror. UV-laser intensities at the sample were estimated to be 1 mW. A computer controlled shutter with an opening time of typically 5 ms was used to locally enhance the fluorescence of GFP.

EXAMPLE 5

Diffusion Analysis

The diffusion analysis was based on the observation that the initial increase in peak fluorescence induced by a laser pulse can be fit by a 2-dimensional Gaussian distribution as follows:

$$F_0(x, y) = C^* \exp(-((x-x_0)^2 + (y-y_0)^2)/a_0^2)$$

with x and y as the pixel values and $F_0$ as the local fluorescence intensity. Sequential images recorded after the UV-pulse were normalized to an averaged image that was recorded before the pulse. The decreased amplitude and the increased radius ($a_n$) of the fluorescence peak in each image was fit by 2-dimensional Gaussian functions as follows:

$$F_n(x, y) = C^*(a_0^2/a_n^2)^* \exp(-((x-x_0)^2+(y-y_0)^2)/a_n^2)$$

Figure 6:
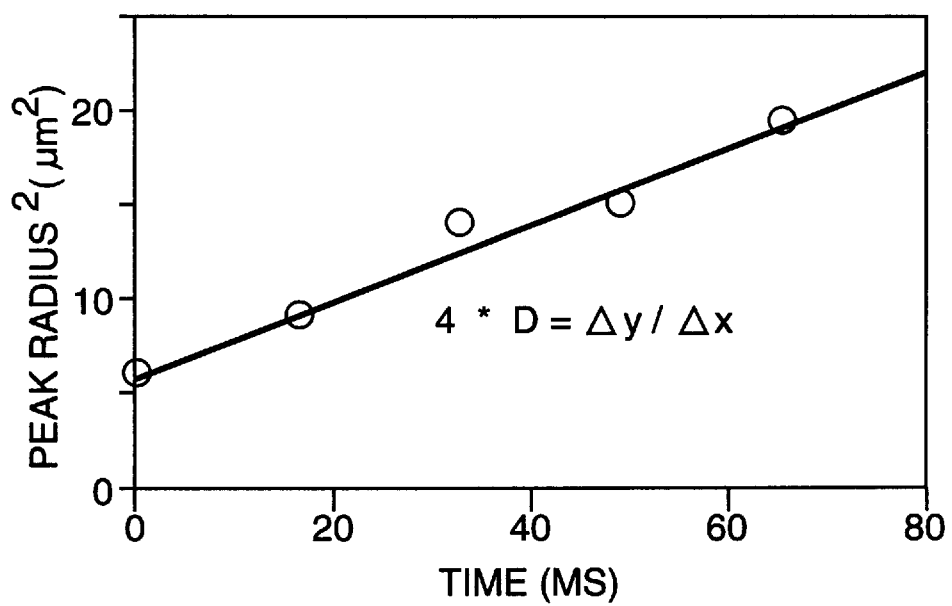
FIG. 6 is a graph illustrating the relationship between the square of the peak radius of GFP as a function of time. This relationship is used in obtaining the diffusion coefficient of GFP.

(assuming mass conservation). A least-squares fit routine was used to determine the radius of each Gaussian peak, $a_n$. The diffusion coefficient was then determined from a graph of the square of the radius, $a_n^2$ versus time (FIG. 6). The diffusion coefficient is directly obtained from the slope of this graph:

$$\Delta y/\Delta x = 4^*D$$

(with D as the diffusion coefficient).

EXAMPLE 6 mRNA Electroporation of Adherent Mammalian Cells

A mRNA electroportion technique for mammalian cells was developed as an alternative to conventional plasmid or viral transduction methods. The strategy underlying this technique involving transcribing RNA in vitro and electroporating the processed mRNA into adherent cells using a small volume electroporation device that uses 1 μL or less of sample volume. The vector used for the in vitro transcription consisted of a 5' untranslated region from *Xenopus laevis* β-globin (see D. Falcone, and D. W. Andrews, *Mol. and Cell. Biol.* 11, 2565–2664 (1991); M. R. Green et al., *Cell* 32, 681–94 (1983)), a Kozak sequence (M. Kozak, *Nucl. Acid Res.* 15, 8125–8148 (1987)), and a GFP insert and a 3' UTR from *Xenopus laevis* β-globin (R. L. Tanguay and D. R. Gallie, *Mol. Cell. Biol.* 16, 146–156 (1996)). In vitro transcription was performed in the presence of a $^7$G(5')ppp (5')G cap analog. High level translation was observed only when a poly(A) tail was added to the RNA in vitro using poly(A) polymerase.

EXAMPLE 7

Translation Efficiency

The translation efficiency of the mRNA construct of Example 6 was tested by measuring the GFP fluorescence intensity of rat basophilic leukemia (RBL) cells electroporated with the in vitro synthesized mRNA. Electroporation of a 3×3 mm region on the coverslip with up to $2 \times 10^4$ cells required 1 μL of mRNA at a concentration of 1 μg/μl.

Figure 3:
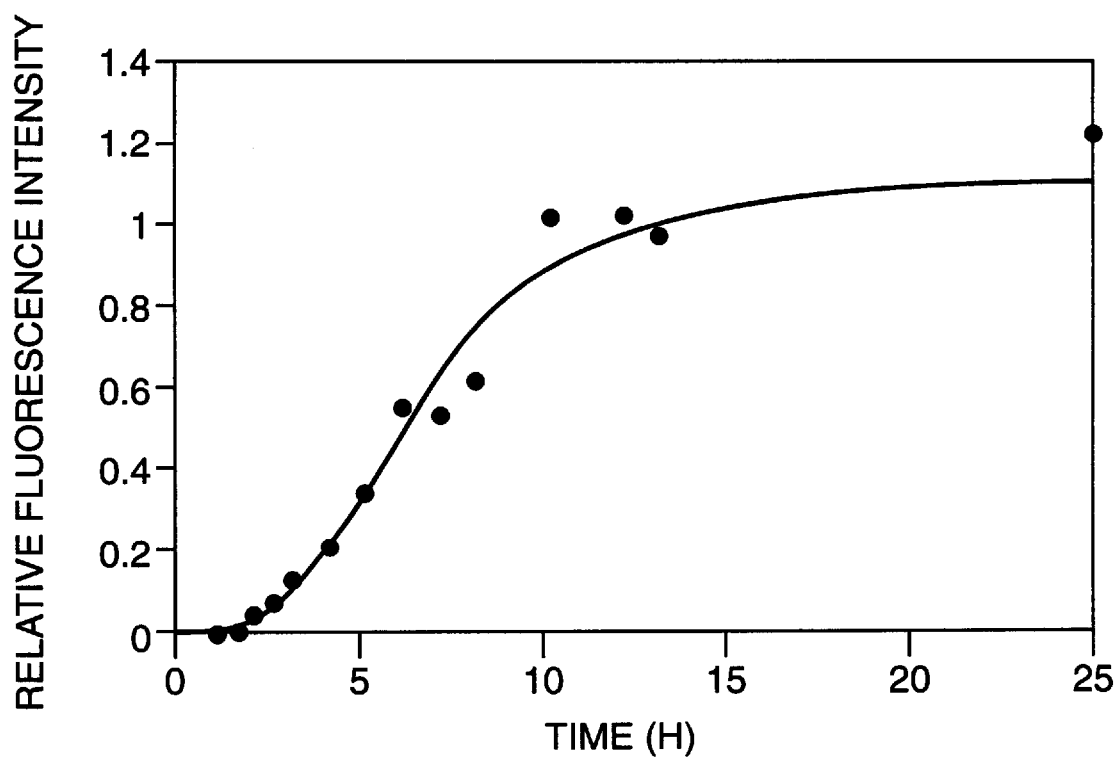
FIG. 3 is a graph illustrating the relative fluorescence intensity of green fluorescent protein (GFP) as a function of time.
Figure 4:
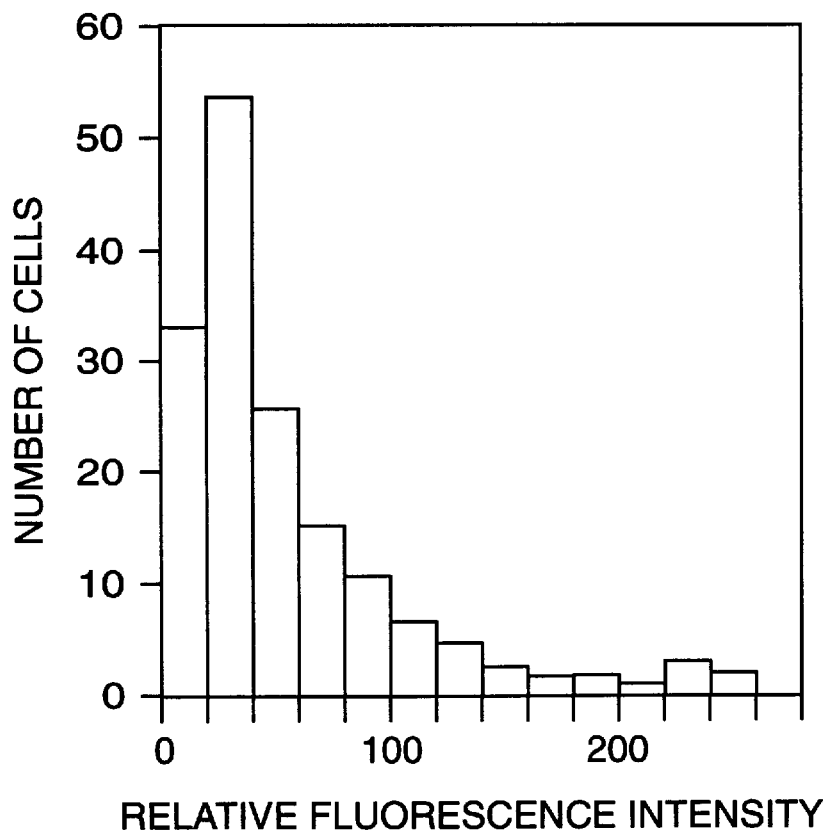
FIG. 4 is a histogram illustrating the relative fluorescence intensity distribution of GFP in RBL cells electroporated with cycle 3 GFP mRNA.

The variability in electroporation of mRNA was quantitatively investigated by measuring the relative fluorescence intensity of GFP in 165 cells and by representing the intensity distribution in a histogram (FIG. 4, measured 10 hours after electroporation). The appearance of GFP fluorescence is nearly linear with time (FIG. 3), except for a 1 hour lag time immediately after electroporation. This lag time is slightly shorter than the 90 minutes required for functional GFP formation, as reported in earlier studies. Cf., A. Crameri et al., supra. GFP fluorescence reached a plateau after 10 hours and remained nearly constant for at least 48 hours. The termination of further fluorescence increase after 10 hours could be explained by the degradation of mRNA and the plateau phase suggests that the expressed GFP is stable for at least 48 hours.

EXAMPLE 8

Fluorescence Enhancement by Spatially Localized UV-laser Pulses

GFP has a main absorbance peak at 395 nm and a smaller peak at 475 nm. M. Chalfie et al., *Science* 263, 802–805 (1994). In vitro studies have previously shown that UV irradiation of GFP at 280 nm leads to a decrease of the 395 nm peak and an increase of the 475 nm peak. A. B. Cubitt et al., TIBS 20, 448–455 (1995). This increase in fluorescence appears to be sustained in vitro. The precise mechanism of the fluorescent enhancement is not yet understood.

The unique photo-isomerization character of GFP was examined to determine whether it could be used to study the spatial dynamics of GFP-tagged proteins in single cells. A UV-laser (365 nm) was coupled into the confocal microscope (488 nm, blue laser line), while the focused UV-laser was used to locally enhance the blue excited fluorescence of GFP within a cell. Depending on the UV-pulse energy, up to a 3-fold increase in local fluorescence was observed. The spatial spreading of the fluorescence after the UV-pulse was analyzed by sequential imaging using a confocal microscope.

EXAMPLE 9

Diffusion Analysis of Wildtype GFP and Cycle 3 GFP

Cycle 3 GFP was originally generated by mutating GFP with a DNA shuffling technique and selecting bacteria with maximal fluorescence intensity. See Crameri et al., supra. In this initial study, it was reported that the high fluorescence of expressed cycle 3 GFP is in part the result of a reduction of the amount of wildtype GFP in inclusion bodies. This report suggested that wildtype GFP may have a hydrophobic surface that causes self-aggregation and is therefore not suitable as a fluorescent tag for protein localization studies.

Figure 5:
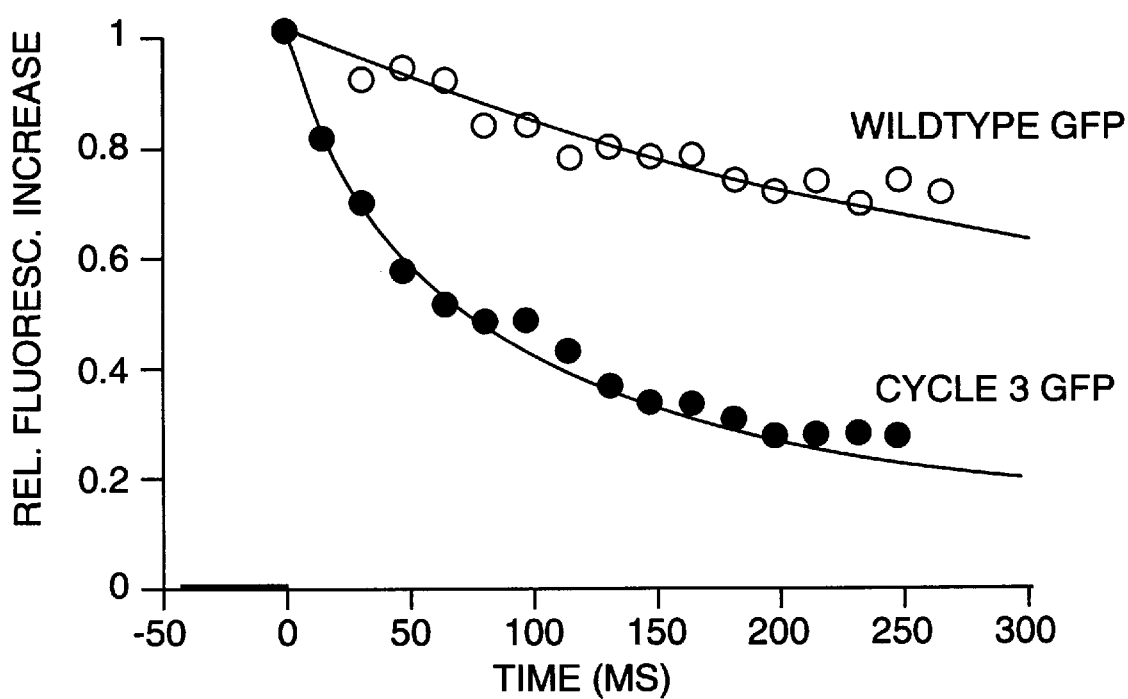
FIG. 5 is a graph illustrating the diffusion-mediated decrease in peak local fluorescence intensity for cells electroporated with wildtype (wt) GFP and cycle 3 GFP mRNA, as a function of time.

This hypothesis was tested by using the local UV-marking technique and directly comparing the mobility of cycle 3 GFP with that of wildtype GFP. FIG. 5 shows measurements of the decrease in peak fluorescence intensity at the UV-laser spot as a function of time. Wildtype GFP is much less mobile than the cycle 3 mutant GFP, suggesting that cycle 3 GFP has less binding interactions in mammalian cells than wildtype GFP.

Figure 7:
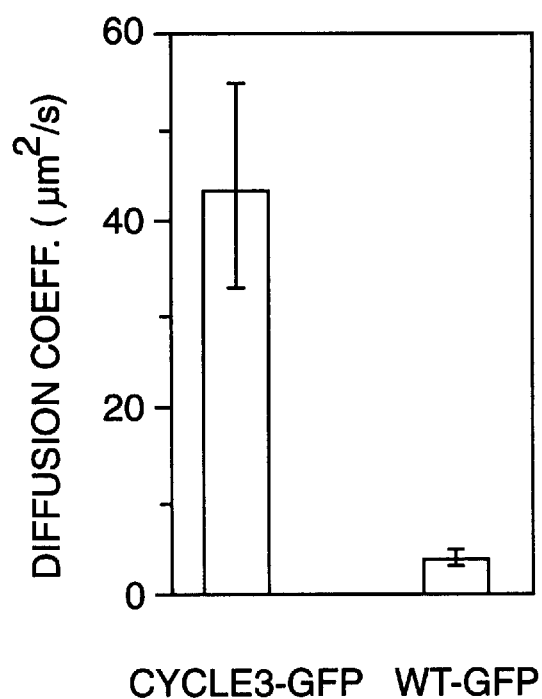
FIG. 7 is a bar diagram illustrating the diffusion coefficients of cycle 3-GFP and wt GFP.

The actual diffusion coefficient of cycle 3 GFP was measured to determine whether its value is consistent with it being a freely diffusing molecule. For this purpose, a 2-dimensional Gaussian distribution was fit to the fluorescence peak in a series of images obtained after the UV-pulse, under the assumption that an ideal diffusion process retains its Gaussian profile over time. A simultaneous decrease in and widening of the peak intensity after the UV-laser pulse was observed. All images were normalized to an averaged fluorescence image recorded immediately before the UV-pulse. The diffusion coefficient of GFP was obtained by graphing the square of the peak radius as a function of time (FIG. 6). Using this analysis, cycle 3 GFP was found to diffuse 10 times faster than wildtype GFP (FIG. 7). The diffusion coefficient of cycle 3 GFP was 43 $\mu m^2/s$ with a standard error of 11 $\mu m^2/s$ (compared to 4.2, $\mu m^2/s$+1.2 $\mu m^2/s$ for wildtype GFP). Thus, cycle 3 GFP appears to be nearly freely diffusible, and is therefore ideally suited as a fusion tag for protein localization studies.

EXAMPLE 10

Expression of Cycle 3 GFP-K-ras Protein (GFP-K-ras)

Immunolocalization and fractionation studies have shown that K-ras (M. S. Boguski, M. S. and F. McCormick, *Nature* 366, 643–654 (1993)), a small GTP-binding protein, is localized to the plasma membrane by a C-terminal farnesyl group and a nearby polybasic region. P. J. Casey, *Science* 268, 221–225 (1995).

mRNA encoding GFP-K-ras fusion protein was microelectroporated into RBL-cells to test the extent of localization of K-ras in intact cells. Fluorescence images showed that K-ras was enriched at the plasma membrane of RBL-cells. While confocal images showed a markedly higher concentration of expressed GFP K-ras fusion protein at the plasma membrane, a lower concentration of GFP could also be observed throughout the cytosol but not inside the nucleus. Such a distribution could be the result of an equilibrium between K-ras bound to the plasma membrane and K-ras diffusible in the cytosol.

EXAMPLE 11

Measurement of the Plasma Membrane Dissociation Rate of K-ras

Figure 8:
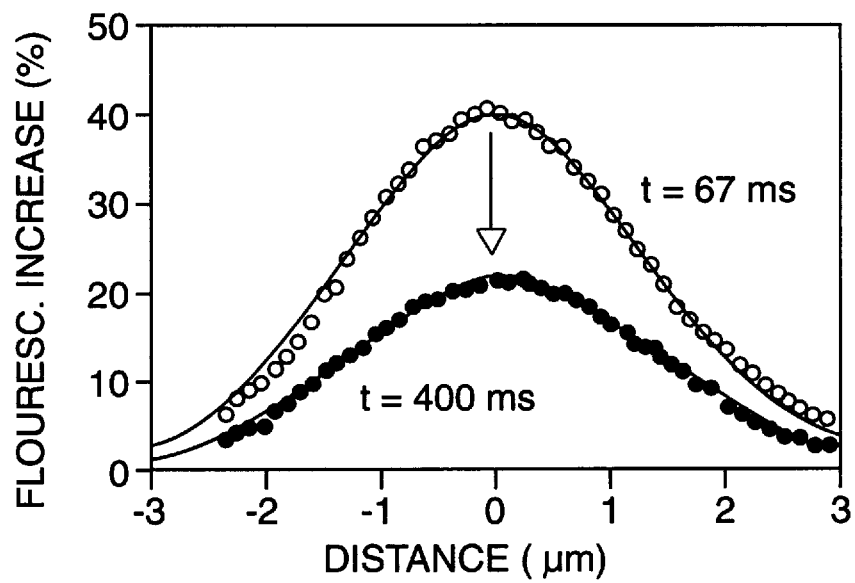
FIG. 8 is a normalized intensity profile of GFP-K-ras electroporated RBL cells at selected times after a plasma membrane-localized UV pulse.
Figure 9:
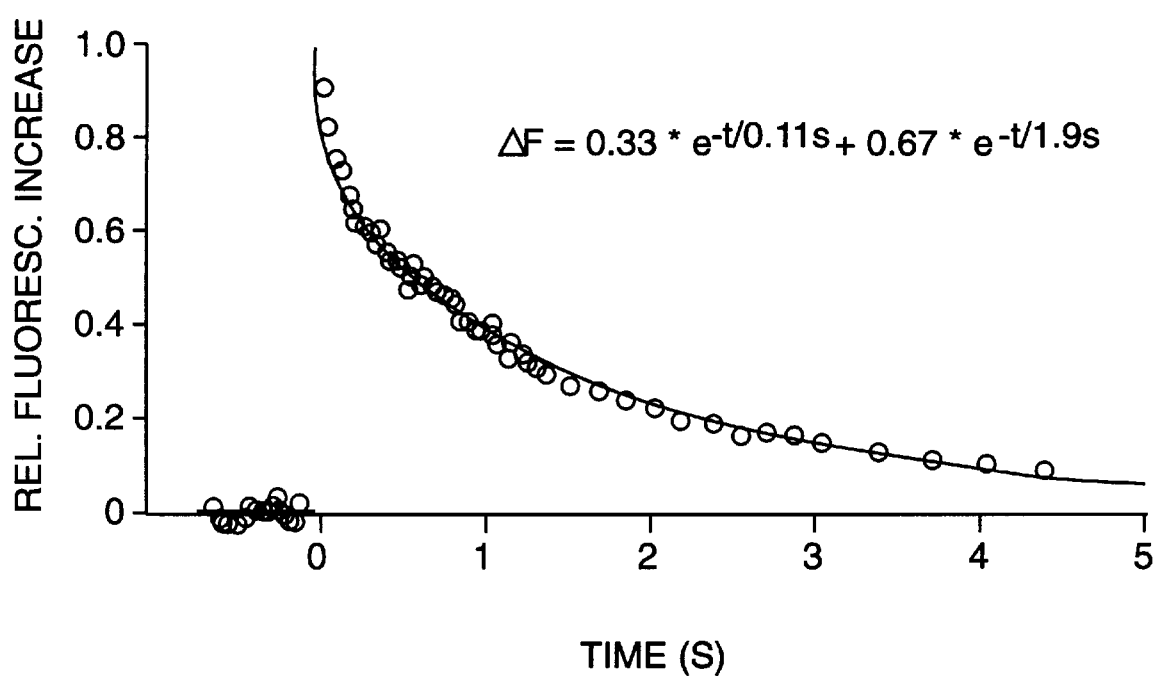
FIG. 9 is a graph illustrating the time course of decrease in local fluorescence of GFP-K-ras localized to the plasma membrane.

UV-laser mediated fluorescence enhancement of plasma membrane localized K-ras was used to test the equilibrium hypothesis of Example 10. Following a UV-pulse, the marked GFP-K-ras rapidly moved away from the focus region as indicated by a decrease in local fluorescence intensity. This decrease in fluorescence was not the result of a lateral diffusion of GFP-K-ras within the plasma membrane, since only a decrease in fluorescence and no widening of the Gaussian-profile could be observed (FIG. 8). Thus, the rapid reduction in local fluorescence must result from K-ras dissociating from the membrane and diffusing away from the plasma membrane as a cytosolic protein. We determined the rate of dissociation of K-ras from the plasma membrane by graphing the decrease in local fluorescence as a function of time (FIG. 9). Re-equilibration between plasma membrane K-ras and cytosolic K-ras occurred on a time scale of a few seconds.

The decrease in fluorescence could be best fit by two time constants of 90 ms±40 ms and 1.5 s±0.7 s, respectively (FIG. 9, N=5). The fast time constant of 90 ms was measured for a small subfraction of the marked GFP and can be explained by the rapid diffusion of cytosolic GFP-K-ras that was close to the plasma membrane and that was also illuminated by the UV-pulse. The 1.5 s time constant would then be the relevant value that describes the dissociation of K-ras from the plasma membrane. Because most plasma membrane K-ras dissociates away from the plasma membrane every 1.5 s, the observed high concentration of K-ras at the plasma membrane and the low concentration in the cytosol can only be sustained if cytosolic K-ras also binds rapidly back to the plasma membrane. Thus, K-ras appears to exist in a dynamic equilibrium and rapidly switches between a plasma membrane bound form and a cytosolic form with a plasma membrane dissociation rate of 1.5 s.

EXAMPLE 12

Measurement of Cell-Wide Fluorescence Redistribution After Local Fluorescence Enhancement or Photobleaching The dynamic equilibrium hypothesis was further investigated by analyzing the fluorescence redistribution across the cell after continued local fluorescence enhancement and continued local photobleaching. An experiment was conducted in which the fluorescence of GFP-K-ras was locally enhanced at the marked location using a series of 20 UV-pulses applied over 2 minutes. Within one minute after local enhancing GFP-K-ras and producing a continued local "source" of enhanced GFP fluorescence, GFP-K-ras was again evenly distributed across the plasma membrane and cytosol as indicated by a cell-wide increase in fluorescence intensity. The laser line of the UV-laser was then switched to its visible lines (mostly 488 nm and 514 nm) for local photobleaching measurements and the same protocol was repeated. Again, within a minute after generating a persistent local "sink" for GFP at the same place, the fluorescence intensity was evenly reduced across the entire plasma membrane and cytosol. It should be noted that no measurable reduction in GFP-K-ras fluorescence intensity could be observed for at least 30 minutes after enhancement, suggesting that the UV-laser mediated fluorescence enhancement is an irreversible or slowly reversible process in intact cells. The results from this local source-and-sink protocol are consistent with a dynamic equilibrium model in which GFP-K-ras rapidly redistributes between a plasma membrane bound and a cytosolic form.

The foreging Examples are illustrative of the present invention, and are not to be construed as limiting thereof.

The invention is defined by the following claims, with equivalents of the claims to be included therein.

That which is claimed:

1. An electroporation apparatus for introducing exogenous material into cells, said apparatus comprising:

a base member configured for holding a cell support, the cell support having a top surface portion, said top surface portion configured for carrying adherent cells;

an electrode carrier operably associated with said base member, said electrode carrier having a bottom surface portion;

a first electrode connected to said electrode carrier;

a second electrode connected to said electrode carrier;

said electrode carrier having a channel formed therein, with said channel positioned between said first electrode and said second electrode, so that said exogenous material may be introduced through said channel and into contact with said cells.

2. An electroporation apparatus according to claim 1, further comprising:

positioning means for maintaining said electrode carrier bottom surface in a spaced relationship to said cell support top surface to define an electroportation chamber therebetween, with said channel formed in said electrode carrier being in fluid communication with said electroporation chamber.

3. An electroporation apparatus according to claim 2, wherein said positioning means is configured for maintaining said electrode carrier bottom surface portion and said cell support top surface portion not more than 500 µm apart.

4. An electroporation apparatus according to claim 2, further comprising a well member having an opening formed therein, with said opening defined by walls configured for receiving said electrode carrier, and with said well member having a bottom surface configured for contacting to said cell support top surface portion, so that said walls enclose said electroporation chamber.

5. An electroporation apparatus according to claim 2, further comprising cushioning means positioned between said base member and said cell support for facilitating the generally parallel orientation of said cell support top surface portion and said electrode carrier bottom surface portion.

6. An electroporation apparatus according to claim 1, wherein said first electrode and said second electrode are generally parallel to one another.

7. An electroporation apparatus according to claim 1, wherein said cell support top surface portion and said electrode carrier bottom surface portion are generally flat.

8. An electroporation apparatus according to claim 1, wherein said first electrode and said second electrode are each members of an interdigitated set of electrodes.

9. An electroporation apparatus according to claim 1, further comprising:

a power supply; and a controller operably associated with said power supply and said first and second electrodes.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CAACGGGCCC AAATGAGTAA AGGAGAAGAA C        31

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCATTTAGGT GACACTATAG        20

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CAACGGGCCC ATATGGCTAG CAAAGGAG        28

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CAACTCTAGA TTATTTGTAG AGCTCATCC        29

( 2 ) INFORMATION FOR SEQ ID NO:5:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:5:

CAACGGATCC ATGACTGAAT ATAAACTTGT G                                          31

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:6:

GTTGGGATCC TTACATAATT ACACACTTTG TC                                         32